(12) United States Patent
Johansson et al.

(10) Patent No.: US 7,935,096 B2
(45) Date of Patent: May 3, 2011

(54) PERCUTANEOUS IMPLANT

(75) Inventors: Martin Johansson, Kungsbacka (SE);
Robert Axelsson, Granna (SE); Anette Johnsson, Jonkoping (SE); Bjorn Edwin, Saetre (NO); Erik Fosse, Oslo (NO)

(73) Assignee: Ostomycure AS, Oslo (NO)

( * ) Notice: Subject to any disclaimer, the term of this patent is extended or adjusted under 35 U.S.C. 154(b) by 316 days.

(21) Appl. No.: 11/218,905

(22) Filed: Sep. 1, 2005

(65) Prior Publication Data

US 2006/0052759 A1    Mar. 9, 2006

Related U.S. Application Data

(60) Provisional application No. 60/615,576, filed on Oct. 5, 2004.

(30) Foreign Application Priority Data

Sep. 6, 2004 (EP) .................................. 04077475

(51) Int. Cl.
*A61F 5/44* (2006.01)
*A61M 5/32* (2006.01)

(52) U.S. Cl. ....................... 604/338; 604/175

(58) Field of Classification Search .............. 604/174, 604/175, 178, 277, 337–344, 317, 327, 328, 604/332
See application file for complete search history.

(56) References Cited

U.S. PATENT DOCUMENTS

| | | | | |
|---|---|---|---|---|
| 3,344,397 A | * | 9/1967 | Elliott et al. ............... | 367/189 |
| 3,451,040 A | * | 6/1969 | Johnson ..................... | 367/183 |
| 3,663,965 A | * | 5/1972 | Lee et al. ................... | 623/23.64 |
| 4,183,357 A | | 1/1980 | Bentley et al. .............. | 128/283 |
| 4,217,664 A | * | 8/1980 | Faso .......................... | 606/108 |
| 4,231,369 A | * | 11/1980 | Sorensen et al. ............ | 604/336 |
| 4,238,845 A | * | 12/1980 | Haggard et al. ............. | 367/183 |
| 4,323,994 A | * | 4/1982 | Coogler ...................... | 367/183 |
| 4,400,861 A | * | 8/1983 | Parker ......................... | 148/518 |
| 4,668,222 A | * | 5/1987 | Poirier ........................ | 604/175 |
| 4,740,876 A | * | 4/1988 | Roller ........................ | 362/390 |
| 4,781,694 A | * | 11/1988 | Branemark et al. ......... | 604/175 |
| 4,897,081 A | * | 1/1990 | Poirier et al. ................ | 604/175 |
| 5,098,397 A | * | 3/1992 | Svensson et al. ............ | 604/175 |
| 5,425,761 A | * | 6/1995 | Lundgren ................... | 623/11.11 |

(Continued)

FOREIGN PATENT DOCUMENTS

GB    2 019 219 A    10/1979

(Continued)

*Primary Examiner* — Nicholas D Lucchesi
*Assistant Examiner* — William Carpenter
(74) *Attorney, Agent, or Firm* — Winston & Strawn LLP

(57) ABSTRACT

A percutaneous implant serves for implantation into an animal or a human body. The implant is of the kind that has an anchoring section, extending radially from a distal end of an interior section. The anchoring section comprises an inner anchoring ring extending from or integral with the interior section, an outer anchoring ring, and at least one connection member for connecting the inner anchoring ring with the outer anchoring ring. Since a first connection point between a first end of the at least one connection member and the inner anchoring ring is angularly offset from a second connection point between a second end of the connection member and the outer anchoring ring, the anchoring section constitutes a resilient spring means, which adapts to the movements of the body. The implant is especially designed for use without externalization of the vessel to be brought into communication with the exterior.

18 Claims, 7 Drawing Sheets

U.S. PATENT DOCUMENTS

| | | | |
|---|---|---|---|
| 5,540,648 A * | 7/1996 | Yoon | 600/114 |
| 5,571,080 A * | 11/1996 | Jensen | 602/56 |
| 6,095,996 A * | 8/2000 | Steer et al. | 602/52 |
| 6,559,350 B1 * | 5/2003 | Tetreault et al. | 602/42 |
| 6,607,504 B2 * | 8/2003 | Haarala et al. | 604/93.01 |
| 6,983,924 B2 * | 1/2006 | Howell et al. | 251/118 |
| 2002/0099344 A1 * | 7/2002 | Hessel et al. | 604/338 |
| 2005/0004526 A1 * | 1/2005 | Reinemann | 604/175 |

FOREIGN PATENT DOCUMENTS

| | | |
|---|---|---|
| GB | 2 045 084 A | 10/1980 |
| WO | WO 98/58691 | 12/1998 |

* cited by examiner

PERCUTANEOUS IMPLANT

This application claims the benefit of U.S. provisional application 60/615,576 filed Oct. 5, 2004.

BACKGROUND

The invention relates to a percutaneous implant for implantation into an animal or a human body.

A method for implantation of the implant according to the present invention into an animal or a human body is also described together with preferred uses.

The implant is of the kind comprising an axial interior section for fixation inside the body, an axial exterior section in communication with the interior section, said axial exterior section extending outwards from the body with a free end, which serves for mounting of a detachable device, the distal end of the interior section opposite the exterior section being provided with an subcutaneous anchoring section, extending radially from the distal end of the interior section.

Many diseases such as e.g., Crohn's disease, ulcerative colitis, intestinal cancer and adenomatous polyposis or bladder cancer require removal of all or part of the intestines or bladder. When the intestines or the bladder are removed, the bodily wastes are expelled through a new surgical opening in the abdominal wall. The surgery to create the new opening, the stoma, is called ostomy. The main steps in the surgery are to create an abdominal opening, to externalize an intestine through the abdominal wall and skin, and suture the intestine to the skin so as to complete the stoma.

The prior art types of intestinal ostomies are performed depending on how much and what parts of the intestines are removed. The surgery is called an ileostomy if the colon and rectum are removed, in which case an ileostomy is performed by attaching the ileum to the stoma. If the rectum is removed, the colon is attached to the stoma to perform a colostomy. Most persons with ostomies must wear special appliances over the stoma and use ostomy pouches to collect and eliminate waste.

A continent ileostomy is the most preferred alternative to using an outside collecting bag. An internal reservoir pouch is created from part of the small intestine. A valve is constructed and a stoma is placed through the abdominal wall. A tube must be inserted through the stoma and the valve in order to drain the pouch from time to time. The most common kind of continent ileoanal reservoir has a capacity of 500 to 1000 mL and a valve made by intussusception of the terminal ileum.

Only for very few patients, ileoanal reservoir surgery is a possible alternative to a permanent ileostomy. Ileoanal reservoir surgery is completed in two surgeries. In the first surgery, the colon and rectum are removed and a pouch or reservoir is constructed from the last part of the small intestine. This pouch is attached to the anus. In the second surgery, the ileostomy is closed. The muscles surrounding the anus and anal canal are left in place, so the stool in the pouch does not leak out of the anus.

Different kinds of urostomy surgery are used dependent on the disease causing the surgery. Usually the ureters are detached from the bladder and joined to a section of the ileum to create an ileal conduit for the urine. One end of this section of ileum is sealed off and the other end is brought to the surface of the abdomen to the stoma to allow urine to be collected in a urine pouch attached around the stoma.

Alternatively, an uretero-cutaneostomy is possible in which the ureters are detached from the bladder and brought to the surface of the abdomen. A uretero-cutaneostomy can be made as a "single" uretero-cutaneostomy in which only one ureter is brought to the surface, a "bilateral" uretero-cutaneostomy with one ureter in each side of the abdomen, a "double-barrel" uretero-cutaneostomy in which both ureters are brought to the same side of the abdomen but externalized using two holes, or a "transuretero" uretero-cutaneostomy in which both ureters are brought to the same side of the abdomen and externalized via one common hole.

The above-mentioned methods are drastic surgical procedures of great discomfort to the patient both before and after surgery is completed.

In summary there are several drawbacks with the above conventional methods including ulceration, incisional hernia, or bulging of the bowel through the incision, narrowing of the stoma, scar tissue and bowel obstruction, marsupialization, avulsion, skin irritation from stool that leaks under the drainage bag and necrosis.

In addition, use of a stoma pouch for collection of the bodily wastes must be used for most ostomies. The stoma pouch is conventionally adhered to the skin by means of an adhesive contact surface on the pouch so as to allow the pouch to surround the stoma for sealingly collecting stool or urine. If liquid secretion penetrates the adhesive surface, this surface will loosen to a certain extent, resulting in leakage from the pouch and the release of an unpleasant smell.

Another problem with ostomies is that the site where the intestine passes the abdominal wall is weak and susceptible to herniation. Hernias result in blockage of the stoma and relief surgery is urgently required.

A number of implants have been provided in order to remedy the above-named disadvantages of the above mentioned prior art systems available today for patients having a stomy.

U.S. Pat. No. 4,183,357 discloses a transcutaneous implant for use with enterostomies. The implant consists of a hollow barrel with a protruding flange, which is permanently positioned under the skin between the dermis and the fascia. The intestine is externalized by drawing the intestine up through the barrel. The barrel surrounds and supports the stoma, however the rigid wall of the implant critically restricts the peristaltic movements.

Similar implant devices for surrounding an enterostomy are disclosed in U.S. Pat. No. 4,217,664 and GB patent No. 2 019 219.

International patent application WO 98/58691 discloses an implant to be used in an intraluminal procedure. A hole is prepared with a purse string suture in the terminated proximal sigmoideum. The plane contact face of the implant is introduced via a colostomy aperture in the abdominal wall and fitted into the prepared aperture in the sigmoideum. The purse string suture is secured and the sigmoideum wall is brought into contact and attached to the parienteral peritoneum surrounding the exterior surface of the implant, the flange part of which is left inside the sigmoideum. The extent of the anchoring zone between the sigmoideum, the peritoneum and the flange is minimal so that fluctuating tensile forces and compressions resulting from peristaltic movements are not restricted. Use of this device involves a high risk of total or partial rupture between tissue and implant, e.g. in case of high back pressure resulting from constipation. Urine or stool may leak and cause inflammation and peritonitis. Thus, improvements in these type devices are desired.

SUMMARY OF THE INVENTION

In a first aspect according to the present invention, a percutaneous implant of the kind mentioned in the opening paragraph is provided, which can be used in ostomy without externalization of a vessel, such as an intestine or a ureter, through the abdominal wall.

In a second aspect according to the invention, an implant is provided, which provides a stable, effective and well vascularized skin-implant junction.

In a third aspect according to the invention, an implant is provided, which is able to conform to and keep pace with any peristaltic movements or mechanical stress.

In a fourth aspect according to the invention, an implant is provided which is not sensed by the patient after implantation, and which can be detachably attached to and disconnected from devices, such as e.g. caps or pouches, thereby giving the surgically treated patient an unprecedented comfort.

In a fifth aspect according to the invention an implant is provided which causes an unprecedented minimum of allergic and inflammatory reaction.

The novel and unique features, whereby this is achieved according to the present invention, is the fact that the anchoring section comprises an inner anchoring ring extending from or integral with the interior section, an outer anchoring ring, and at least one connection member for connecting the inner anchoring ring with the outer anchoring ring.

The problem of establishing a leak proof zone between the implant and the enterostomy is solved according to known prior art implants by either entirely enclosing the externalized vessel or by placing at least a part of the implant inside the lumen of the vessel. In contrast, the implant according to the present invention is situated on top of the vessel wall. For example, if the vessel to be brought in fluid communication with the exterior is the small intestine, the lower face of the anchoring section can be placed directly on the selected spot on the fascia above the intestinal serosa and secured in situ, e.g. by means of sutures, tissue glue or staples. The exterior section of the implant is externalized through an access hole in the abdominal wall and the upper face of the anchoring ring is brought into contact with the epithelium of the peritoneum and secured in a similar manner as the lower face of the anchoring section. Finally the contact zone is left to heal up. In this simple manner the vessel and peritoneum covering the fascia is fused together in the area adjacent the anchoring section. Gradually, a natural, strong adherence is spontaneously generated between the implant, vessel, and peritoneum.

The anchoring section ends up infiltrated with vascularized connective tissue, which ensures that a strong, and reliable attachment level between the wall of the vessel, the peritoneum/fascia, Mm. abdominis and the implant can be obtained. The access opening in the vessel may be created at any time during the procedure to finally allow the stool to escape. Scar formation can be kept to a minimum and only the intestinal mucosa will, as usual, be in direct contact with stool. Accordingly the risk of inflammation and/or infection is also minimal.

When a first connection point between a first end of the at least one connection member and the inner anchoring ring is angularly offset from a second connection point between a second end of the connection member and the outer anchoring ring, the rings together with the connection members act as an axially resilient, circumferential spring means, which is able to respond to any movements and/or to absorb shear of the implant in relation to the adjacent organs, without damaging the established, biological connective tissue adherences.

In a preferred embodiment the inner diameter of the outer anchoring ring is greater than the outer diameter of the inner anchoring ring. The radial distance between the rings contributes to the flexibility and resiliency of the anchoring section, but also the chosen material and the material thickness are of significant importance to flexibility.

Preferably, the at least one connection member is S-shaped. Said S-shape has shown to provide the anchoring section with a high level of requisite resiliency. A main part of the connective tissue is created and integrated in the gaps between the components of the anchoring section and this connective tissue fusion constitutes in co-operation with the rings an elastic coupling of the implant to the body when the patient and/or the organs or implant move beyond control of the patient.

In one advantageous embodiment according to the present invention the anchoring section extends at an angle of approximately 90-110°, preferably 90° from the interior section, so as to substantially follow the curvature of the internal abdominal wall at the area of the access site in said abdominal wall.

A seal and connection of the anchoring section between the intestinal serosa and the epithelium of the peritoneum can be easily obtained if at least one of the inner anchoring ring, the outer anchoring ring and the at least one connection member is provided with through-going transverse openings. Such openings may have different sizes and allow for ingrowths of connective tissue and subsequent vascularization of the created connective tissue.

It is further preferred that at least one of the inner anchoring ring, the outer anchoring ring or the at least one connection member has a cross-section with rounded edges, preferably a substantially circular cross-section, to form a smooth tissue junction between the connective tissue which traverses and surrounds the respective components of the implant.

Rounded edges have the important advantage that no cutting action occurs when the implant moves slightly in response to organ movements and physical action of the person wearing the implant. The risk of avulsion is further prevented by means of this design.

Yet a further and very important advantage of rounded edges over edged edges is the fact that the new tissue, which is gradually created around parts of the anchoring section and through the through-openings, is enabled to create a solid, fluid-proof seal between implant parts and surrounding tissue, especially the accessed intestine.

For this reason it is most preferred that all of at least one of the inner anchoring ring, the outer anchoring ring or the at least one connection member has a cross-section with rounded edges.

In case the surgeon prefers to use tissue glue for attachment of the anchoring section to the vessel, said tissue glue may be advantageously applied in advance to at least one surface on the anchoring section. For example the said surface may be coated with a biologically acceptable tissue glue, optionally covered by a peelable foil, so that the implant is easy to maneuver inside the body without sticking to unintended sites during attempt to place the implant correct in situ.

Commercially available tissue glues are known to the person skilled in the art of surgery and may e.g. be selected from the group consisting of cyanoacrylates, fibrin sealants or combinations of these. Fibrin sealant is a non-toxic, biological product that can stimulate wound healing and reduce hospital stay.

A sheet of mesh, such as e.g., monofilament polypropylene mesh, having approximately the same size as the area of the lower anchoring face defined by outer periphery of the anchoring section, can advantageously be provided on and cover the lower face of the anchoring section. The mesh can be glued to any part of the lower face of the anchoring section not provided with through-going transverse openings and serves as a sealing material between fascia and anchoring section.

In a preferred embodiment according to the present invention the mesh is firmly adhered by means of biological acceptable glue to both the elongated connection members and the part of the axial interior section defined by the distal wall thickness.

A central portion of the mesh has a radius, which corresponds approximately to the radius of the inner anchoring ring of the implant. This central portion is saturated with the biological acceptable glue, which in solidified condition provides a fluid barrier across the total thickness of the mesh at the entire radial distance of the central portion. This barrier is effective as a seal in the area of contact between implant, mesh and fascia. None of the through-going transverse openings in the implant are covered or filled with glue. Accordingly, tissue in-growth and vascularization conditions are excellent.

The central portion can preferably have a central guiding hole for guidance of the trocar of a surgical cutting and stapling device, thus ensuring correct position of the surgical cutting and stapling device. A suitable device is designed for in a first step carefully penetrating the respective layers to be anastomosed. In the second step a circular section is cut out in one single operation of the pressed together layers of overlaying layers of glue saturated mesh, fascia, peritoneum and intestinal wall to provide an outlet opening which allow the content of the vessel to escape freely into the bore of the implant for disposal when required. Simultaneously the surgical cutting and stapling device staples the created circumferential walls of the holes of the glue saturated mesh, fascia, peritoneum and intestinal wall sealingly together with the inner anchoring ring and the mesh. The healing process including tissue in-growth and vascularization, is initiated by the natural mechanism. Surgical cutting and stapling device devices are commercially available and will not be described in greater detail here. Various suitable surgical cutting and stapling devices for use in the surgical procedure according to the present invention is obtainable from e.g. Ethicon Endo-Surgery, Inc., 4545 Creek Road, Cincinnati, Ohio 45242, USA.

A suitable device is selected according to the required diameter of the stoma. As an example of suitable devices can be mentioned various sizes of Proximate ILS, straight Intraluminal Stapler, from Ethicon Endo-Surgery Inc.

The solidified and integrated glue structure of the central portion of the mesh has the further advantage of stiffening the central portion thereby promoting proper and fast identification of the guiding hole by the trocar of the surgical cutting and stapling device for further penetration through fascia, peritoneum and intestinal wall.

The presence of the sealing material effectively prevents fluid, which flows in the accessed vessel, e.g. an intestine, from leaking in between the joined layers of various tissues and implant. The mesh further promotes strong tissue in-growth and body acceptability of the implant and reduces time of healing.

The central portion can in an alternative embodiment be made of another type of mesh having a closed pore structure and is thicker than the rest of the central portion.

Also a tissue mesh is foreseen within the scope of the present invention. A preferred tissue mesh is an autograft.

The implant according to the present invention is made of at least one biologically acceptable material. Preferably the implant is made of titanium, due to the strength, workability and biological acceptability, but other materials or combinations of materials recognized within the art are also within the scope of the present invention. Other biologically acceptable material materials or combinations of materials are foreseen within the scope of the present invention. E.g. the implant can be made of a polymeric material solely or of two materials of different hardness, e.g., polymeric material-metal. The polymeric material can e.g. be a thermosetting and the metal e.g. NITINOL® or the above mentioned titanium.

BRIEF DESCRIPTION OF THE DRAWINGS

The invention is described in more detail below, exclusively describing examples of embodiments with reference to the drawing, in which.

DETAILED DESCRIPTION OF THE PREFERRED EMBODIMENTS

Figure 1:
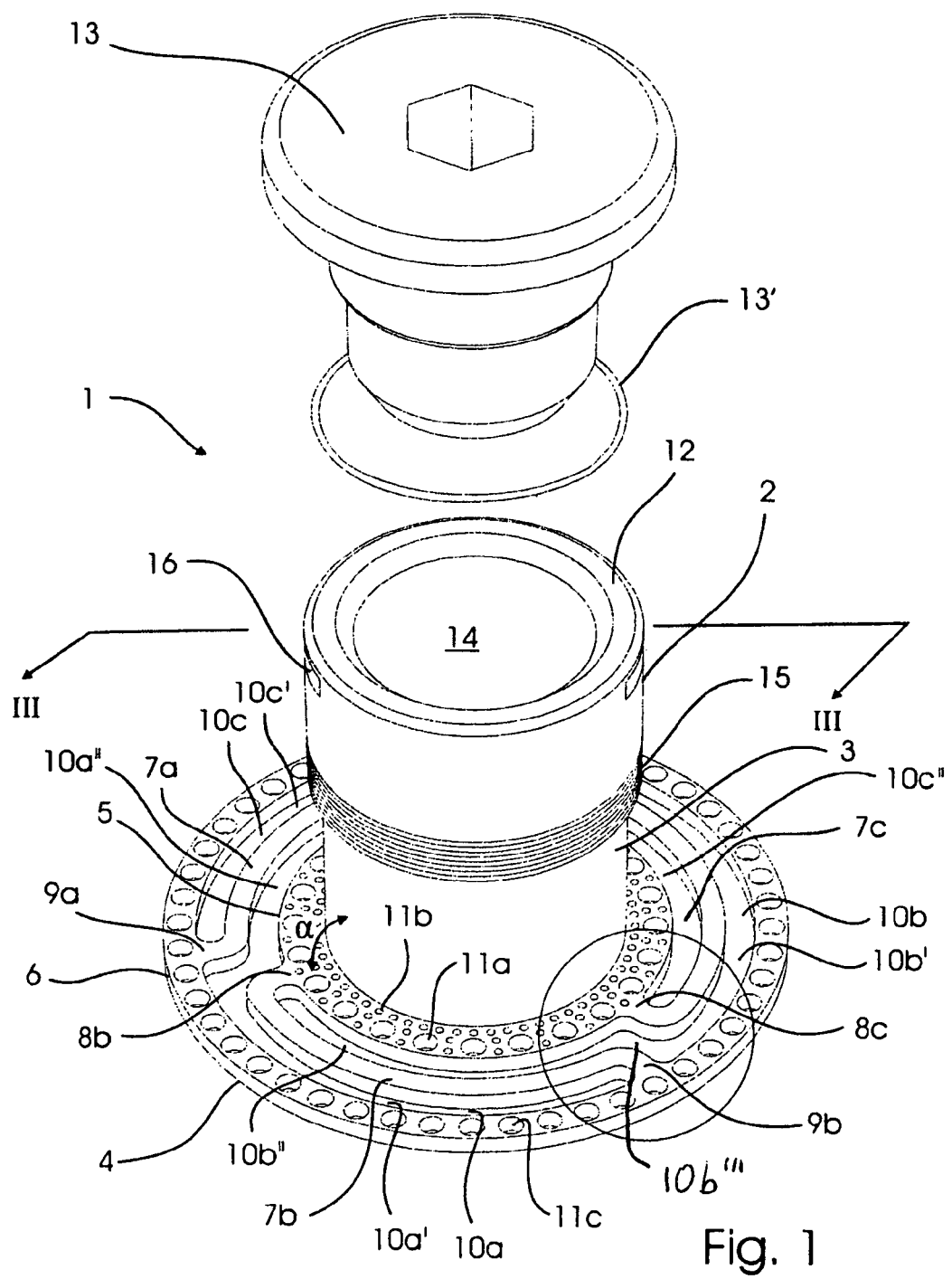
FIG. 1 shows, in perspective, an implant according to the present invention and a closure plug for insertion into the bore of the implant.
Figure 2:
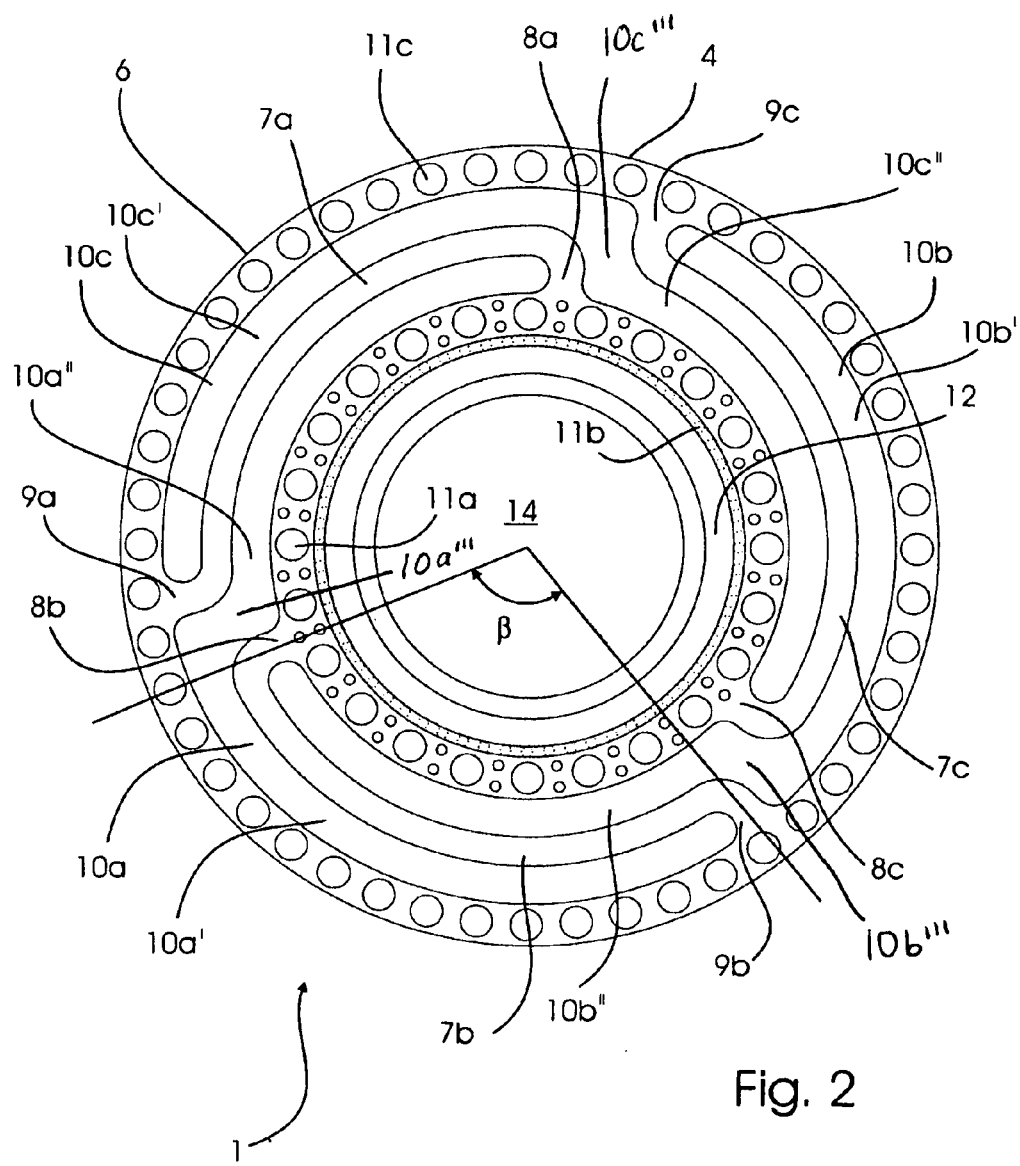
FIG. 2 shows a top view of the implant according to the present invention.

The implant shown in FIGS. 1 and 2 is in its entirety designated with reference number 1. The implant 1 is only by way of an example shown in the drawing implanted in relation to the ileum, however the use with any other vessel is intended within the scope of the present invention.

FIG. 1 shows an implant 1 with an axial exterior section 2, an axial interior section 3, from which an anchoring section 4 extends radially in an angle α of approximately 90°. The anchoring section 4 consists of an inner anchoring ring 5, an outer anchoring ring 6 concentric with the inner anchoring ring 5 and three elongated connection members 7a,7b,7c for connecting the inner anchoring ring 5 with the outer anchoring ring 6. As seen best in FIG. 2 the connection member 7b is connected at a substantially right angle to the inner anchoring ring 5 at a first connection point 8b, and at a substantially right angle to the outer connection ring 6 at a second connection point 9b. In a similar manner the connection members 7a,7c are connected to the rings 5,6.

The connection points 8a,8b,8c between the connection members 7a,7b,7c and the inner anchoring ring 5 are circumferentially, angularly offset from the connection points 9a,9b, 9c between the connection members 7a,7b,7c and the outer anchoring ring 6 at an angle β. The substantially right connection angle and the angular offset β give the connection members substantially an S-shape. However, within the scope of the present invention the connection members can be connected to the rings at different angles α, such as e.g. an acute angle of 45°.

The outer anchoring ring 6 has a greater diameter than the inner anchoring ring 5. The circumferentially, angularly offset joining of the rings 5,6 obtained by means of the connection members 7 delimit elongated circumferential gaps 10a, 10b,10c between the rings 5,6. The combination of gaps 10 and connection members 7 provide the desired resiliency of the anchoring section 4 in order for this section to absorb external stresses acting on the skin and the implant keeping the internal region free of stress.

The inner 5 and outer anchoring ring 6 have a plurality of through-going transverse openings 11a,11b,11c with identical or different diameters. The openings 11 serve for ingrowth of connective tissue and vascularization.

In addition, in a preferred embodiment some of the openings 11 are used as suturing holes when the ileum, fascia and peritoneum are to joined, e.g. by means of sutures, to allow healing and formation of connective tissue.

The axial exterior section 2 extends outwards from the body with a free end 12, which is adapted for mounting a detachable device, such as a closure plug 13, a cap or an ostomy pouch (not shown).

When the closure plug 13 is inserted in the tubular bore 14 of the implant 1, stool is prevented from being expelled. The lumen of the externalized intestine serves as a temporary reservoir and must be emptied from time to time. The peristaltic movements promote emptying. Alternatively conventional irrigation means can be used to assist emptying of stool accumulated in the intestinal reservoir.

The axial exterior section 2 is furthermore provided with a plurality of circumferential ribs 15, intended for promoting firm mechanical securing of the exterior section to the surrounding tissue. Furthermore the ribs impede downgrowth of epithelium.

The exterior section may furthermore be equipped with various coupling means for the properly sealed attachment of caps and pouches. Such means include but are not limited to recesses or indentations, O-rings, snap-fitting means, bayonet coupling means, locking rings etc.

Figure 3:
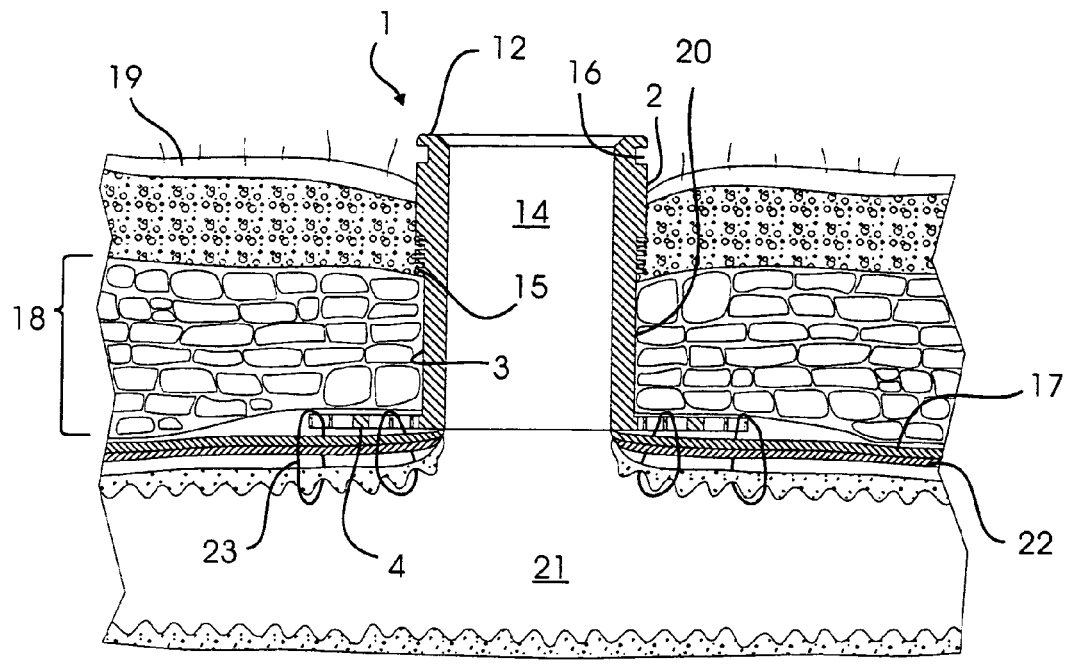
FIG. 3 shows a section of the implant of FIG. 1 taken along the line III-III. The implant is seen schematically in a first implantation step immediately after implantation according to a first embodiment of a surgical procedure.

A surgical procedure is now described by way of example with reference to FIG. 3.

The first step in the surgical procedure is to make a first vertical incision through the abdominal wall down to the fascia 17. This incision is made approximately 5-10 cm from the site where the implant 1 is to be located. Next the fascia 17 is separated from the Mm. abdominis 18 by dilatation to create a gap for the later introduction of the implant 1 and permanent location of the anchoring section 4 between fascia 17 and Mm. abdominis 18.

An access hole 20 for the implant 1 is surgically created through the skin 19 and further through the detached tissue layers 18 of the abdominal wall by means of punching, cutting and blunt dissection, taking precautions not to penetrate the intestine 21 at this early surgical step.

The required surgical procedure, e.g. removal of a malfunctioning or diseased section of the intestine, optional refashioning of the intestine to create a reservoir such as e.g. a Koch's reservoir, and closure of any intestinal residues left in situ, is then performed.

Now the implant 1 is introduced via the first incision into the created gap between the fascia 17 and the Mm. abdominis 18. The axial exterior section 2 is passed through the access hole 20 such that the free end 12 protrudes a small distance from the body. The anchoring section 4 is placed directly on the fascia 17 above the spot on the intestine 21, which is to be brought into communication with the exterior via the bore 14 of the implant 1. To avoid displacement of the implant 1 in relation to the intestine 20 and abdominal tissue, including the fascia 17 and the peritoneum 22, different kinds of attachment means and systems can be used.

Optionally, the outer wall of the axial exterior section 2 including the ribs 15 may be further secured to the wall of the access hole 20 by means of tissue glue or sutures (not shown) if necessary.

An import aspect is to create a superior tight connection between tissues and implant.

By creating a superficial lesion on the exterior outside of the intestinal wall and optionally a corresponding superficial lesion on the epithelium of the peritoneum, so as to enhance inclination to produce natural adherences, the natural tendency to create adherences is advantageously utilized. Since the fascia in an early surgical step is separated from Mm. abdominis, both fascia and Mm. abdominis are lesional and strongly inclined to grow together again. Consequently, a natural strong connective tissue adherence, which keeps the implant in situ, and which connects the intestine with the implant and the adjacent tissue can be established by natural healing procedure in a very simple manner.

In one embodiment, as seen in FIG. 3, the implant 1 is initially combined with the relevant section of the intestine 21 and the fascia/peritoneum 17;22 by means of a number of sutures 23 through at least some of the plurality of holes 11a,11c of the inner anchoring ring 5 and the outer anchoring ring 5, respectively. Optionally, any tissue overlaying the upper face of the anchoring section 4 can also be secured to the implant by means of said sutures 23 (or other sutures) if appropriate to avoid preliminary dislocation of the implant 1. Eventually the sutures 23 will dissolve or be digested by the body.

Figure 4:
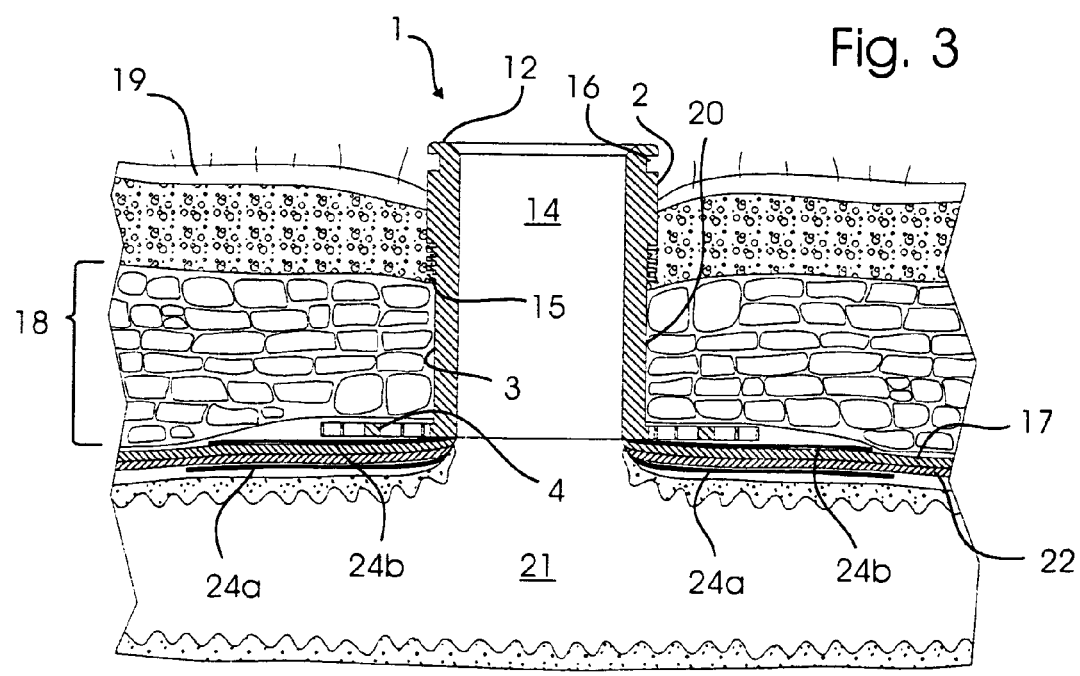
FIG. 4 shows the same but the implant is implanted according to a second embodiment of a surgical procedure.

In a second embodiment, as seen in FIG. 4, the sutures 23 are substituted by tissue glue layers 24a, which attach the lesional serosa of the intestine to the epithelium of the peritoneum 22, and tissue glue layer 24b, which attaches the lower face of the anchoring section 4 to the fascia 17. Optionally, the upper face of the anchoring section 4 can also be glued to adjacent tissue. Such tissue glue is very suitable for performing a highly strong joining of biologically acceptable components, and will be absorbed eventually leaving a tight pressure resistant vascularized skin-implant junction. The glue may be applied either on the tissue or on a surface of the implant. In a very simple embodiment the glue may also be precoated on the implant.

The outlet opening in the ileum 21 is made whenever appropriate via the access opening 14 of the implant 1 using e.g. a scalpel or another other appropriate surgical cutting tool.

Figure 5:
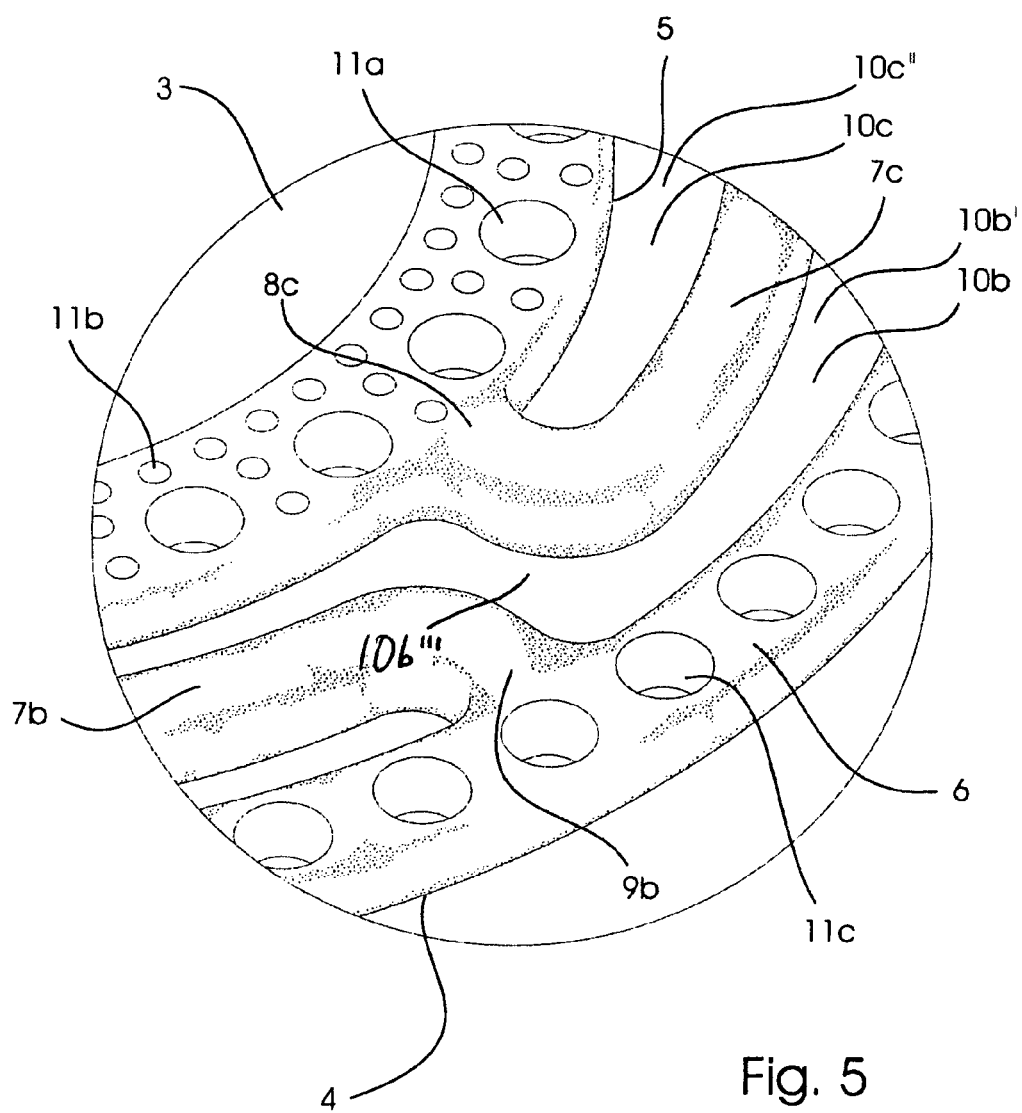
FIG. 5 shows on an enlarged scale a perspective view of a detail of a modification of the anchoring section seen in FIG. 1.

A detail of a preferred embodiment of the implant according to the present invention is shown in FIGS. 1 and 2 and in enlarged scale in FIG. 5. A plurality of S-shaped connection members extend from the inner ring 5 to the outer ring 6 and delimits elongated circumferential gaps 10a, 10b, 10c between the inner anchoring ring and the outer anchoring ring wherein each gap circumferentially extends from one S-shaped connection member's second connection point 9a, 9b, 9c on the outer anchoring ring 6 to define a first gap part 10a', 10b', 10c' each having a first radius. The gaps 10a, 10b, 10c extend to a second gap part 10a'', 10b'', 10c'' of a subsequent circumferential S-shaped connection member's first connection point 8a, 8b, 8c on the inner anchoring ring 5. The first and second gap parts are connected by way of a transition 10a''', 10b''', 10c'''. A shown, the second gap parts 10a', 10b', 10c' have a second radius that is smaller than the first radius of the first gap part 10a', 10b', 10c'. The rounded edges of the components of the anchoring section 4 ensure that the cutting action from the edges of the components of the implant is eliminated. In addition a strong seal of connective tissue can form around and conform to said components. Especially preferred is a circular cross-section of the connection members 7.

Figure 6:
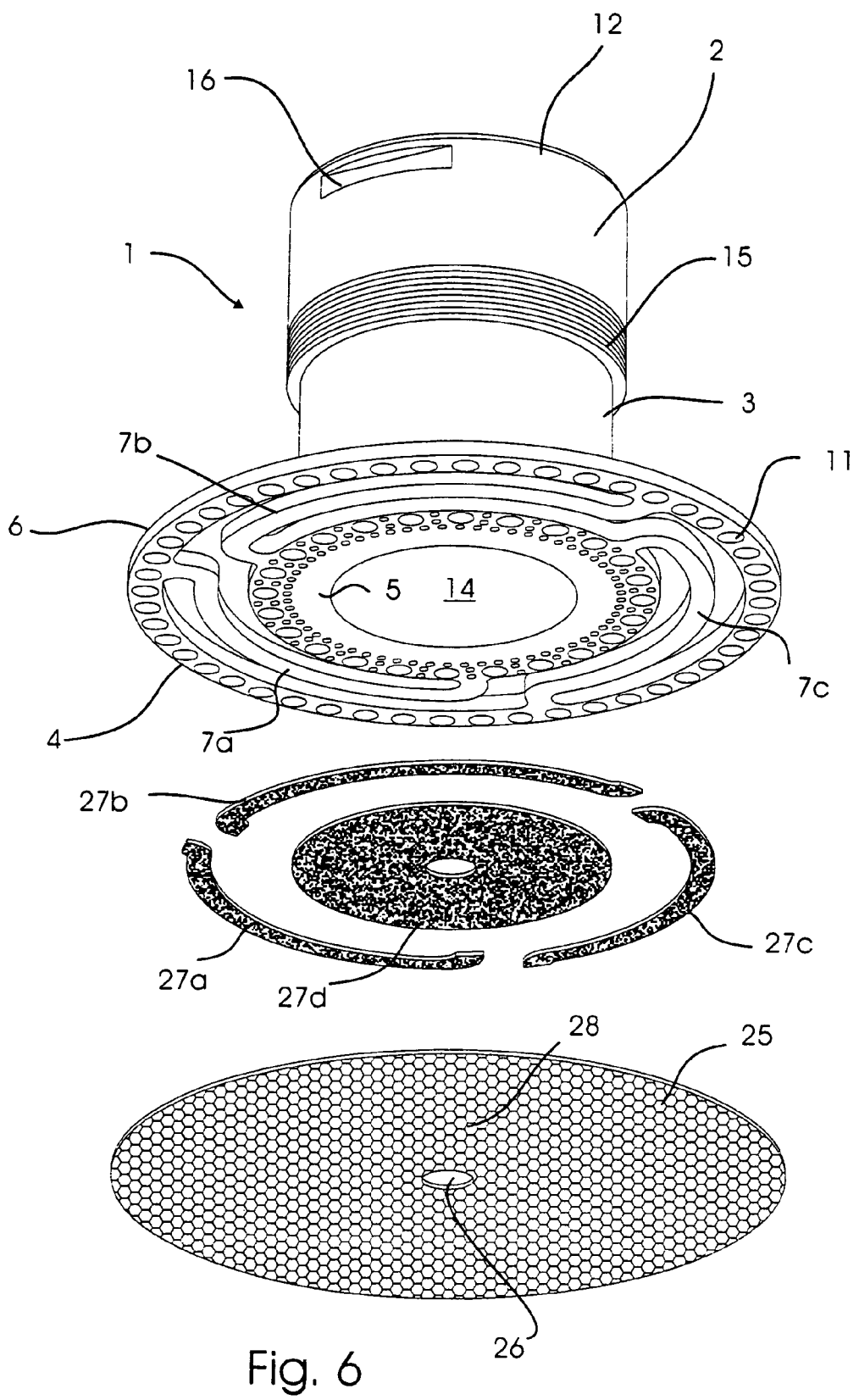
FIG. 6 shows in an exploded view the lower face of the implant of FIG. 1 provided with a sealing mesh; the locations of the glue applications are indicated separately.
Figure 7:
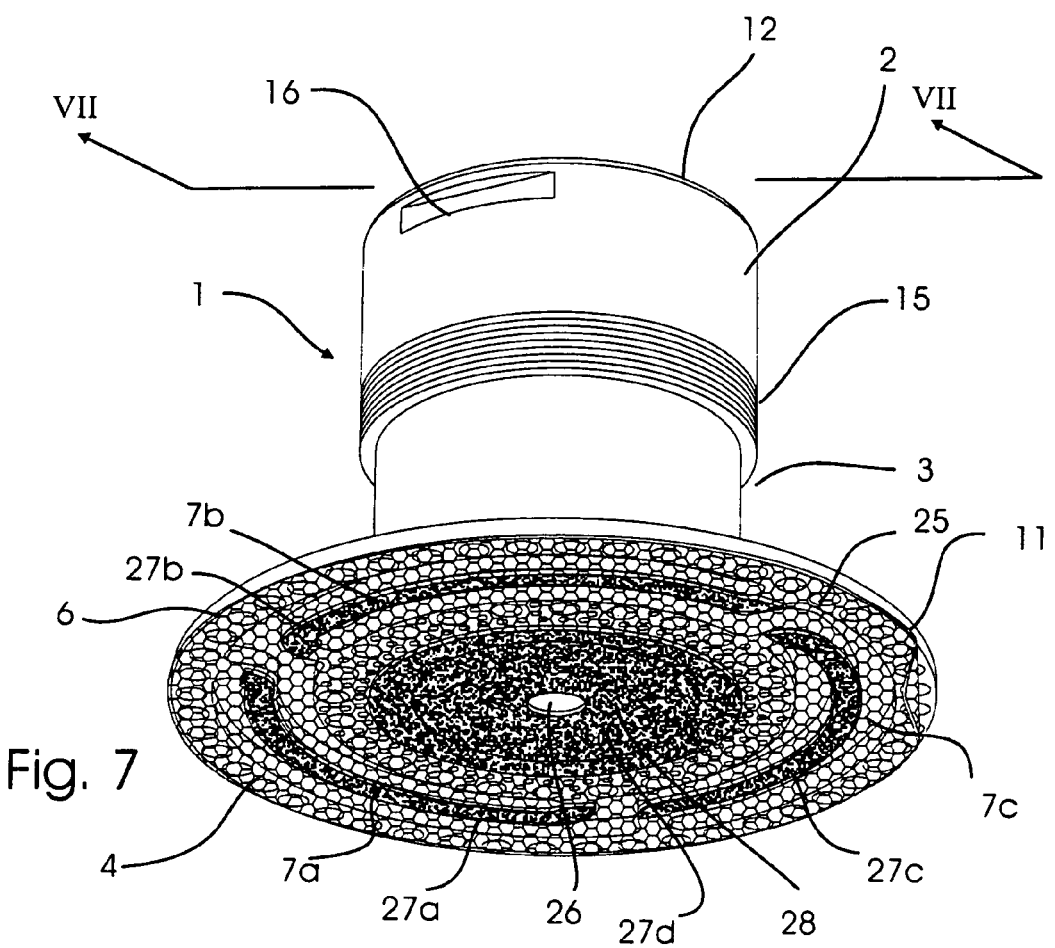
FIG. 7 shows the embodiment shown in FIG. 6 in a position ready for implantation.

An especially preferred modification of the embodiment of the implant according to the present invention shown in FIG. 1 is shown in FIGS. 6 and 7.

In the exploded view of FIG. 6 a circular mesh 25 with a guiding hole 26 are provided on the entire anchoring section 4, as seen best in FIG. 7. The mesh 25 has an open pore structure.

By means of a biological acceptable glue 27d,27a,27b,27c, the circular mesh 25 is adhered to only the inner anchoring ring 5 and the elongated connection members 7a,7b,7c, respectively.

Figure 8:
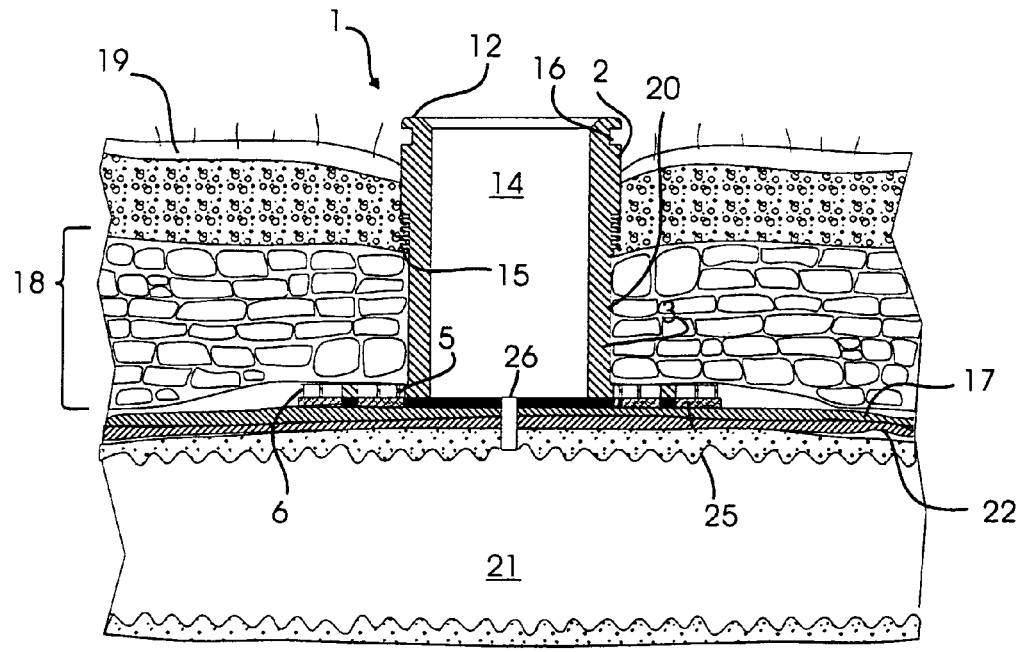
FIG. 8 shows a section of the implant of FIG. 7 taken along the line VII-VII. The implant is seen schematically after implantation on top of an intestinal vessel in a first step of a surgical implantation procedure using a conventional cutting and stapling device.

The glue cake 27d fills the pore structure of the central portion 28 of the mesh 25 as seen best in FIG. 7. The initial step of implantation of this embodiment corresponds to the embodiment shown in FIG. 3. The subsequent procedure is described above and illustrated in the sectional views of FIGS. 8 and 9 demonstrating securing the implant to the subjacent layers by means of staples. The same numerals are reused for like components.

The staples 29 have the advantage that conventional available surgical instruments can be used as described above. They are known to the surgeon, easy to use and the entire securing of the implant is done within minutes. Furthermore, the staples 29 squeezes and holds the mesh 25, the fascia 17, the peritoneum 22 and the wall of the intestine 21 firmly and sealingly tight together during the healing, preventing fluid from penetrating in between these components and layers. The risk of irritation and inflammation is thereby considerably reduced.

Figure 9:
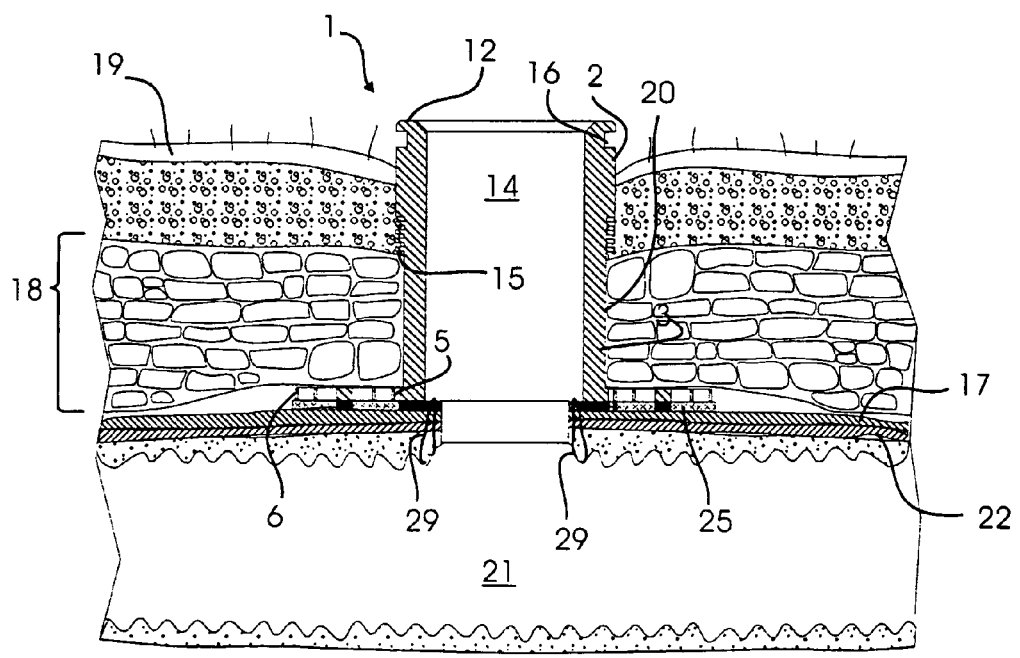
FIG. 9 shows the same in a third step of the surgical implantation procedure.

As can be seen from FIG. 9 the circumferential wall of the cut-out extend a small distance into the bore of the implant to establish a small protrusion for the staples. In case the circumferential protrusion is of inconvenience to the patient the protrusion and the staples can easily be removed as soon as a sealingly tight and firm attachment is ensured.

Securing of the anchoring section 4 on top of the fascia 17 can be made using any of the means sutures, glue, staples and any appropriate combinations of these means.

The first incision is closed and precautions may be taken not to put extensive load on the surgical structure for the first few days after surgery. In order not to stress the healing procedure and put pressure on the connection between any tissue and the implant, stool must be allowed to escape freely during an initial period during which the patient may be equipped with a conventional ostomy pouch. In addition a diet can be prescribed, e.g., an astronautic diet for reducing stool formation.

Eventually, when the adherence between organs, tissue and implant has been proved strong enough, the plug 13 can be placed in the bore 14 of the implant 1. Whenever appropriate, the plug 13 is removed in order to drain the reservoir of the externalized intestine 21. Disposable plugs 13 may be preferred by some patients. An O-ring 13' can be provided around the plug 13 to further ensure air and liquid sealing capability.

In most cases there is no need to create an intestinal reservoir since the intestinal wall will itself adapt to the new conditions and develop a pressure resistant thickened wall.

The surface characteristics of the implant are important to facilitate and improve healing with connective tissue. In order to give a surface roughness that promotes interaction and healing with tissue the proximal exterior section is in a preferred embodiment brightly polished and the distal exterior section, the interior section and the anchoring section are blasted, preferably with aluminum oxide, or coated with surface coating.

It is further preferred to provide each implant with a unique identifier to be able to trace the implant and problems that might relate to production, e.g. choice of material and design, and to collect and record relevant data in an anonymous manner. The implant can be made very small and since various collecting and closure devices can be detachably attached to the free end of the exterior section of the implant, bodily waste can be expelled when and where it is appropriate. The patient is offered a hitherto unknown degree of freedom to behave and live an almost normal life.

What is claimed is:

1. A percutaneous ostomy implant for implantation into an animal or a human body, comprising:

an axial interior section for fixation inside the body, an axial exterior section in communication with the interior section and extending outwards from the body with a free end, said free end of the exterior section serving for mounting of a detachable device and a distal end of the interior section opposite the exterior section is provided with an anchoring section, extending radially from the distal end of the interior section, wherein the anchoring section comprises an inner anchoring ring extending from or integral with the interior section, an outer anchoring ring, and at least one connection member for resiliently connecting the inner anchoring ring with the outer anchoring ring, and wherein a first connection point between a first end of the at least one connection member and the inner anchoring ring is angularly offset with an angle β from a second connection point between a second end of the connection member and the outer anchoring ring, wherein the at least one connection member is S-shaped extending from the inner ring to the outer ring in a plane therebetween to provide axial resilience and anchorage to the anchoring section and delimits elongated circumferential gaps between the inner anchoring ring and the outer anchoring ring, wherein a gap circumferentially extends from one S-shaped connection member's second connection point on the outer anchoring ring to define a first gap part having a first radius to another subsequent circumferential S-shaped connection member's first connection point on the inner anchoring ring, which has a transition to a second gap part having a second radius that is smaller than the first radius of the first gap part; and wherein the inner diameter of the outer anchoring ring is greater than the outer diameter of the inner anchoring ring.

2. An implant according to claim 1, wherein the anchoring section extends from the distal end of the interior section at an angle α of approximately 90-110°.

3. An implant according to claim 1, wherein the anchoring section extends from the distal end of the interior section at an angle α of approximately 90°.

4. An implant according to claim 1, wherein at least one of the inner anchoring ring, the outer anchoring ring or the at least one connection member is provided with through-going transverse openings.

5. An implant according to claim 1, wherein at least one of the inner anchoring ring, the outer anchoring ring or the at least one connection member has a cross-section with rounded edges.

6. An implant according to claim 1, wherein at least one of the inner anchoring ring, the outer anchoring ring or the at least one connection member has a substantially circular cross-section.

7. An implant according to claim 1, wherein a lower face of the anchoring section is covered with a polypropylene or tissue mesh.

8. An implant according to claim 7, wherein the mesh is adhered to the inner anchoring ring and the elongated connection members by means of a biological acceptable glue.

9. An implant according to claim 7, wherein the mesh has a central portion which is either of a different pore structure or a different thickness than the rest of the mesh or is saturated with glue.

10. An implant according to claim 7, wherein the mesh has a central portion which is of a different pore structure and a different thickness than the rest of the mesh.

11. An implant according to claim 10, wherein the central portion of the mesh is saturated with glue.

12. An implant according to claim 9, wherein the central portion has a guiding hole.

13. An implant according to claim 1, wherein at least one surface on the anchoring section is coated with a biologically acceptable tissue glue.

14. An implant according to claim 13, wherein the anchoring section and glue are covered by a peelable foil.

15. An implant according to claim 13, wherein the tissue glue is selected from the group consisting of cyanoacrylates, fibrin sealants or combinations of these.

16. An implant according to claim 1, wherein the implant is made of at least one biologically acceptable material.

17. An implant according to claim 1 wherein three S-shaped connection members are present, each extending from the inner ring to the outer ring in the plane therebetween.

18. A percutaneous ostomy implant for implantation into an animal or a human body, consisting essentially of:
    an axial interior section for fixation inside the body,
    an axial exterior section in communication with the interior section and extending outwards from the body with a free end, said free end of the exterior section serving for mounting of a detachable device and
    a distal end of the interior section opposite the exterior section is provided with an anchoring section, extending radially from the distal end of the interior section,
    wherein the anchoring section comprises an inner anchoring ring extending from or integral with the interior section, an outer anchoring ring, and three S-shaped connection members for connecting the inner anchoring ring with the outer anchoring ring, and
    wherein for each connection member, a first connection point between a first end of the connection member and the inner anchoring ring is angularly offset with an angle β from a second connection point between a second end of the connection member and the outer anchoring ring, with each S-shaped connection member extending from the inner ring to the outer ring and having a first end portion connected to the inner ring, a second end portion connected to the outer ring and a central arcuate portion resiliently and concentrically located between the inner and outer rings in a common plane therebetween to provide axial resilience and anchorage to the anchorage section, and with the connection members delimiting elongated circumferential gaps between the inner anchoring ring and the outer anchoring ring, wherein each gap circumferentially extends from one S-shaped connection member's second connection point on the outer anchoring ring to define a first gap part having a first radius to another subsequent circumferential S-shaped connection member's first connection point on the inner anchoring ring, which has a transition to a second gap part having a second radius that is smaller than the first radius of the first gap part;
    wherein the anchoring section extends from the distal end of the interior section at an angle α of approximately 90-110°, the inner diameter of the outer anchoring ring is greater than the outer diameter of the inner anchoring ring; and a lower face of the anchoring section is covered with a polypropylene or tissue mesh.

* * * * *